United States Patent [19]

Schmidt

[11] 3,986,534

[45] Oct. 19, 1976

[54] DEVICE FOR MEASURING AND DISPENSING FRACTIONARY VOLUMES OF LIQUID SAMPLES

[75] Inventor: Jean Michel Schmidt, Orgeval, France

[73] Assignee: Intertechnique S.A., Plaisir, France

[22] Filed: June 2, 1975

[21] Appl. No.: 582,764

[30] Foreign Application Priority Data

July 30, 1974 France .............................. 74.26426

[52] U.S. Cl. ...................................... 141/1; 141/34; 23/253 R; 195/104; 195/140
[51] Int. Cl.² ....................... B65B 3/04; C12K 1/10
[58] Field of Search ................. 141/31, 34, 54, 57, 141/58, 59, 99, 100, 234, 236, 283, 285, 286, 297, 312, 325, 329, 330, 331, 332, 363, 369, 370, 392, 245, 1, 9, 11; 222/319; 233/26; 23/293, 299; 195/140, 104, 127, 139, 139 LE

[56] References Cited

UNITED STATES PATENTS

| 3,766,016 | 10/1973 | Guigan | 141/34 |
| 3,770,027 | 11/1973 | Guigan | 141/34 |

*Primary Examiner*—Houston S. Bell, Jr.
*Attorney, Agent, or Firm*—Lane, Aitken, Dunner & Ziems

[57] ABSTRACT

A device for measuring and dispensing fractions of a liquid sample comprises a casing having a vertical axis and containing a central chamber and transparent cells distributed around the chamber. Each cell is connected to the chamber by a closure cup. A capillary constriction separates each pocket from the corresponding cell. The device may be used for the preparation of antibiograms.

14 Claims, 6 Drawing Figures

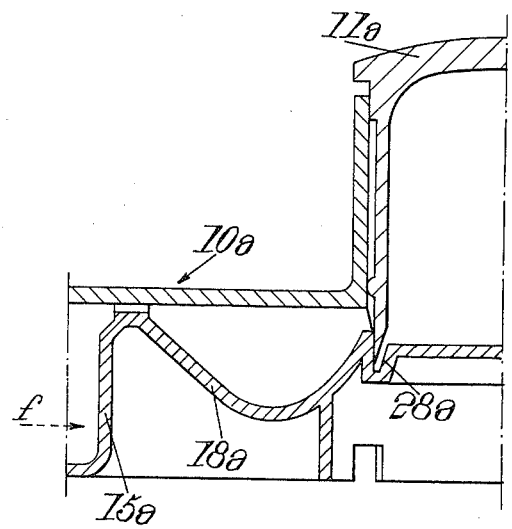
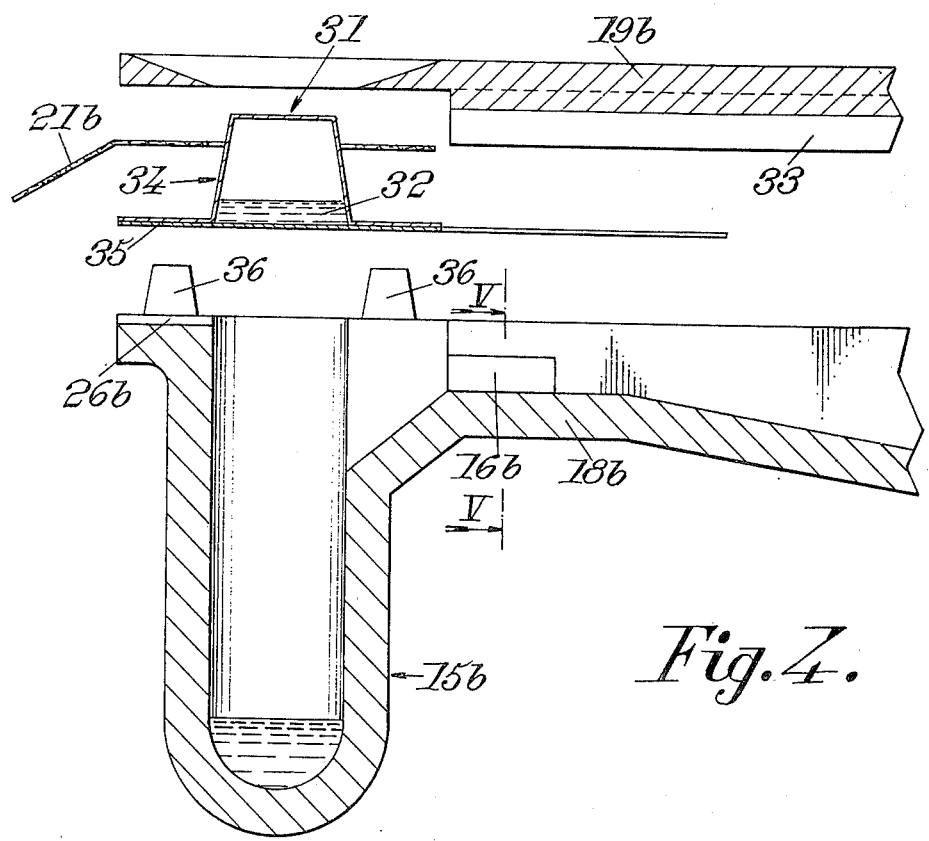

DEVICE FOR MEASURING AND DISPENSING FRACTIONARY VOLUMES OF LIQUID SAMPLES

BACKGROUND OF THE INVENTION

The present invention relates to devices for measuring predetermined volumes of a liquid sample and possibly subjecting said volumes to analytical operations.

Previously distributing devices have been developed in which a liquid sample in a storage vessel is distributed among a number of tubes. The distributing device of U.S. Pat. No. 3,770,027 (Guigan) comprises a vertical central tube formed with apertures and connected to a number of test tubes by capillary tubes provided with a constriction. When a liquid storage vessel is slid over to the bottom part of the tube, liquid enters capillary tubes to the constriction therein due to capillary action. When the storage vessel is withdrawn, the portion of liquid sample still in the vertical tube flows down, whereas the portions in the capillary tubes remain inside them. The liquid in each capillary tube can then be spun into a corresponding test tube, simply by rotating the device at a speed sufficient to overcome the capillary forces.

That device is of relatively simple construction. On the other hand, it has drawbacks which are particularly serious when the device is used to distribute samples of infections, noxious or dangerous liquids, e.g. preparations of micro-organisms. The vertical tube remains upwardly and downwardly open after the storage vessel has been removed while it communicates with the filled capillary tubes. The fractions may flow and contaminate the environment if the device is upset or handled carelessly while taken to the centrifuge. The balance of liquid contained in the storage vessel may also be spilled inadvertently. The volume contained in a capillary tube is insufficient for many analytical applications. Due to the small volume of the tubes, it is difficult to construct a device of the afore-mentioned kind wherein the differences in volume between the capillary tubes is negligible as compared with the volume of the tubes.

Another prior art device (U.S. Pat. No. 3,606,083) is similar but includes an annular chamber formed on the upper surface of a disk. Again, there is a substantial risk of spill over. In addition, the liquid which remains available in the annular chamber refills the capillary tubes after the device has been spun to empty the tubes and has come to rest again.

Other known devices for obtaining fractions of samples use centrifugal force to distribute liquid samples from a central well. Devices of this kind are described inter alia in "A miniature fast analyzer system" in Analytical Chemistry, Vol. 45, No. 3, March 1973, pp. 328A–339A.

These device comprise a rotor in which the centrifugal force sprays fractions of a sample from a central well into lateral chambers. Again, that device is not accurate enough for a number of uses.

SUMMARY OF THE INVENTION

An object of the invention is to provide a novel device for obtaining fractions of predetermined volume of a liquid sample and for transferring it to test cells or tubes.

A further, more specific, object of the invention is to provide a device which is useful for testing susceptibility of bacteries contained in a liquid sample to different antibiotics.

According to an aspect of the invention, there is provided a device comprising an axially vertical casing having an axis which is kept vertical in operation, an axial upwardly open chamber arranged to receive said liquid sample and a plurality of test cells having transparent walls distributed around said chamber, and a plurality of pockets each having an end communicating with said chamber and located to be filled by liquid flowing from said chamber and another end communicating with a respective one of said cells via a capillary constriction, and closure means arranged to separate said chamber from said pockets and to retain said volumes in said pockets when inserted into said casing.

The term "capillary constriction" is used to mean a passage which is of such size as to prevent the sample liquid from flowing therethrough when subjected to a hydrostatic pressure corresponding to a liquid head of a few centimeters. On the other hand, the constriction should have dimensions such that the sample liquid can be spun out into the cells when the liquid is subjected to an acceleration exceeding about 10 times the gravitational acceleration. The flow path of the liquid through the constriction should be such that the centrifugal acceleration, when the device is rotated, has a component which tends to drive the liquid out of the pockets. The flow path will typically be approximately radial with respect to the axis of the device.

Advantageously, each pocket is laterally bounded by vertical walls which are substantially parallel and radially directed and are at a distance not exceeding a few millimeters (1 to 5 mm in most cases). The top wall of each pocket can be flat, horizontal or slightly sloping, to prevent the capture of bubbles which would result in inaccuracies of measurement. The lower wall is typically concave towards the top, over most of its extent at least.

The closure means may be cup-shaped and formed to be suitable as a vessel to supply the sample to be divided into fractions. The side wall of the closure means may be shaped to cooperate with the lateral wall of the cylindrical central chamber, either by forcefitting or by a threaded connection. The contents of the pockets can be isolated by forcing the edge of the cup wall against the lower wall of the chamber. The terminal edge of the side wall can be convex or knife-edged and can engage in a circular groove at the bottom of the chamber for sealingness. Alternatively, the side wall of the chamber can be provided with access apertures to the pockets, in which case the side wall of the cup may also be provided with apertures adapted to be placed opposite the access apertures, depending on the angular position given to the cup.

The invention has numerous applications, more particularly in medicine and biochemistry and, more generally, when the volumes have to be analysed using different reagents. The reagents, in dried or lyophilised form if necessary, can be placed beforehand in the cells. In the case, for example, where antibiograms by dilution in a liquid medium are to be obtained, the reagent may be a culture medium containing the antibiotic whose effect is to be measured, and a colour indicator, e.g. a pH indicator. A similar approach may be used for identifying strains of micro-organisms.

Since the cells have transparent walls, the analytical results can be determined visually or, more accurately, using a photocolorimeter which can operate automatically. Photocolorimeters of known types can be used whenever a positive reaction is shown by a colour change in the body of liquid in the cell. If the cells have parallel surfaces, it is simply necessary to convey each cell in turn between a suitable source of light (for instance yellow light at 380 nm wave length in the case of antibiograms) and a suitable detector, which is disposed behind an optical filter if necessary. If a positive reaction is shown only by turbidity, the latter can be detected by absorption of light at a longer wavelength, e.g. approx. 650 nm.

The invention will be better understood from the following description of embodiments thereof, which are given by way of non-limitative examples.

BRIEF DESCRIPTION OF THE DRAWINGS

FIG. 3 is similar to FIG. 1 and shows a modified embodiment;

FIG. 4 is a view on an enlarged scale showing a cell and the accompanying components of a device according to a modification of the device in FIG. 1, before assembly;

DESCRIPTION OF PREFERRED EMBODIMENTS

Figure 1:
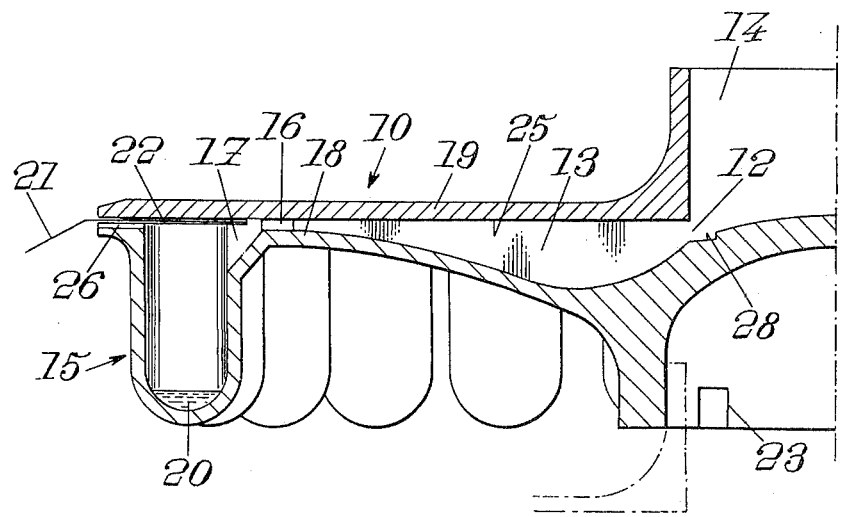
FIG. 1 is a simplified elevation view of the device, partly in cross-section along a vertical plane, with the closure means removed.
Figure 2:
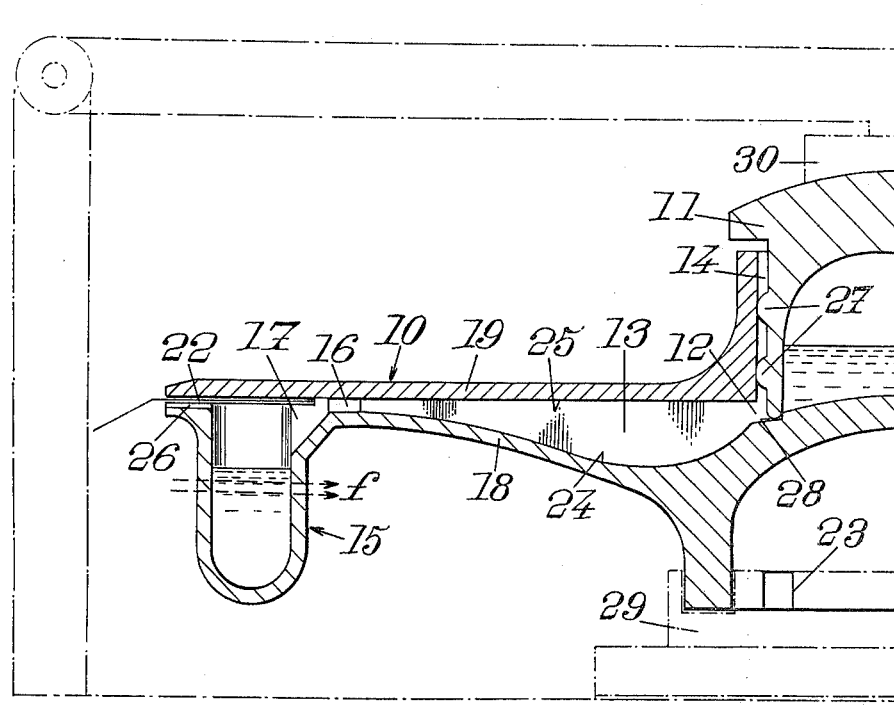
FIG. 2 shows the device of FIG. 1 after fractions of a sample have been transferred into analytical cells, the device being disposed on a centrifuge used for spinning the fractions into the cells of the pockets.

Referring to the drawings, FIGS. 1 and 2 show diagrammatic representation of a device for obtaining fractions of a liquid sample; the device comprises a casing 10, consisting of several assembled components and removable closure means 11. The casing has a substantial rotational symetry around an axis which is located vertically during use. The casing contains a central chamber which opens upwardly and has a capacity varying from a few milliliters to a few tens of milliliters. The chamber is connected via lateral apertures 12 to a number of pockets 13 formed in the casing, regularly distributed around the central chamber and extending substantially radially. Each pocket is associated with an analysis cell 15 in the form of a test-tube having a transparent side wall. A constriction 16 is provided between each pocket 13 and the corresponding cell 15, the transverse dimensions of each constriction being such that it is capillary for the liquid to be divided into fractions (of course the liquids can have greatly variable surface tensions). The connecting passage 17 provided between each constriction 16 and the corresponding cell 15 is flared so as to prevent the liquid in pockets 13 from seeping along the wall to cells 15.

The casing 10 in FIG. 1 comprises a bottom plate 18 and a top plate 19 force-fit into one another. The bottom plate 18 forms the bottom of chamber 14, and the bottoms and side walls of pockets 13 and cells 15 (24 cells being provided in the embodiment illustrated).

Since the cells walls must be transparent, all of plate 18 is advantageously made of a plastic material which is transparent over a wide range of optical frequencies, which is rigid and which can be shaped by moulding. It can be made of crystal polystyrene, which withstands most conventional chemical reagents. The moldable plastic material sold under the TM DIACON and comprising methylmetacrylate and polystyrene may also be used.

The top plate 19 forms the side wall of chamber 14, the top walls of pockets 19 and the covers of cells 15. It can be made of the same material as the top plate or of a material which is more flexible than that of the bottom plate, so as to facilitate force fitting. It may be made inter alia of polypropylene or polyethylene. The plates may be shaped so that the casings can be stored by stacking, as indicated by the chain-dotted lines in FIG. 1.

The casing shown in FIG. 1 contains a layer of reagent 20 at the bottom of each cell 15. In the case of a device for obtaining antibiograms, the reagent may be e.g. a culture medium containing a specific antibiotic and a colour indicator, e.g. a pH indicator.

Advantageously, a label 21 is disposed opposite each cell so as to identify each antibiotic. All the labels can be carried by a single flexible ring 22 secured between plates 18 and 19. In addition, an identification notch 23 can be formed in the lower skirt of plate 18 so that it can be mounted in only one angular position on a data-reading device.

A narrow slot 26 connects each cell to atmosphere, so that air can escape from it and the liquid can flow into it.

Advantageously, each pocket is flat in the vertical direction; to this end, the bottom plate has slits having vertical, parallel and substantially radial walls and spaced apart by 1 to 5 mm. The bottom 24 of each slot curves smoothly and is advantageously concave along its first part from the central chamber. The top wall 25 of the pockets may be flat and horizontal or slightly conical downwards or upwards, so as not to trap bubbles. In the resulting casing, all the pockets can have the same volume. Preferably, the two plates are not secured by gluing at the constrictions, since drops of glue may block the constrictions or reduce their cross-section.

The device also comprises a closure member 11 (FIG. 2) which can be made of moulded material, e.g. the same material as plate 19. In the embodiment shown in FIG. 2, the side wall of the closure means 11 has beads 27 which are forced into the side wall of the cell, so that when the closure member has been completely pressed down it is retained in position. The terminal edge of the side wall of means 11 is rounded and bears against the bottom of a groove 28 formed at the bottom of the chamber so as to separate the interior thereof from pockets 13.

Closure member 11, which is cup-shaped, can be given a sufficient capacity for use as a storage vessel for containing the liquid sample and transferring it to the casing.

A way of operating the device according to the invention will now be described, in the case where antibiograms are prepared.

A liquid sample, is prepared, comprising a dilute solution of bacteria, the sensitivity of which is to be determined against various antibiotics in the device. The volume of sample need not be precisely determined, provided that it is sufficient to fill all the pockets. The sample is poured into the central chamber 14, from where it flows into the pockets, which it fills up to the constrictions 16. Next, the closure member 11 is positioned so as to separate the contents of pockets 13 (which form a corresponding number of pipettes) from the liquid remaining in chamber 14. When the closure means is in position, the dilute solution of bacteria cannot contaminate the environment. Furthermore, if the closure means is used as a conveying cup, there is no additional contaminated vessel to be discarded and destroyed.

Next, the device is placed on the rotating part of a centrifuge, which can be manual or driven by a motor at a given speed of rotation. FIG. 2 diagrammatically shows the device on top of the rotating part 19 of a centrifuge, the outline of which is shown by broken lines. The centrifuge frame has an arm bearing on closure member 11, the arm being sufficiently heavy to prevent the device from moving during centrifuging. A conventional centrifuge can be used. The electric motor is energized by a timing device so that the centrifuging conditions are reproducible. If the device has a diameter of approx. 10 cm, a speed of a few tens of r.p.m. is sufficient.

After the contents of each pocket 13 has been transferred into the corresponding cell 15, the device is placed in an incubator. It is shaped so that it can easily be placed horizontally. After a certain period, usually about one day, the date are read, either visually or, advantageously on an automatic photocolorimeter which may be conventional and comprises a light source (e.g. a light emitting diode) which directs a radial light beam $f$ (FIG. 2) onto a suitable detector.

The photocolorimeter can operate stepwise, bringing each cell in turn between the source and the detector and holding it there for the necessary time. Alternatively, the number of detectors can be equal to the number of cells, although the latter method is expensive. Still other methods may be used.

The closure means 11 shown in FIG. 2 has a side wall with a rounded terminal edge. In the modified embodiment illustrated in FIG. 3, on the other hand, closure means 11a is a cup having a knifeblade terminal edge which engages in a correspondingly shaped groove 28a formed in the bottom plate 18a. For increasing the surface traversed by the light for colorimetry, the cells 15a are typically located adjacent each other, without any gap between successive cells, and of substantially rectangular horizontal cross section.

The device can be used inter alia to prepare a wide variety of antibiograms from a small-volume sample, each pocket usually having a capacity less than 100 microliters and each circular row being easily capable of containing 36 cells with an overall diameter of 8 cm. The cells can contain antibiotics at different concentrations and different combinations of antibiotics. A plurality of devices can be provided and used in succession, a first device being used to determine the antibiotics towards which the strain is active or resistant, and a second device (whose cells contain different concentrations of the same antibiotics) being used to determine the minimum inhibiting concentration (CMI) of the active antibiotics.

Figure 6:
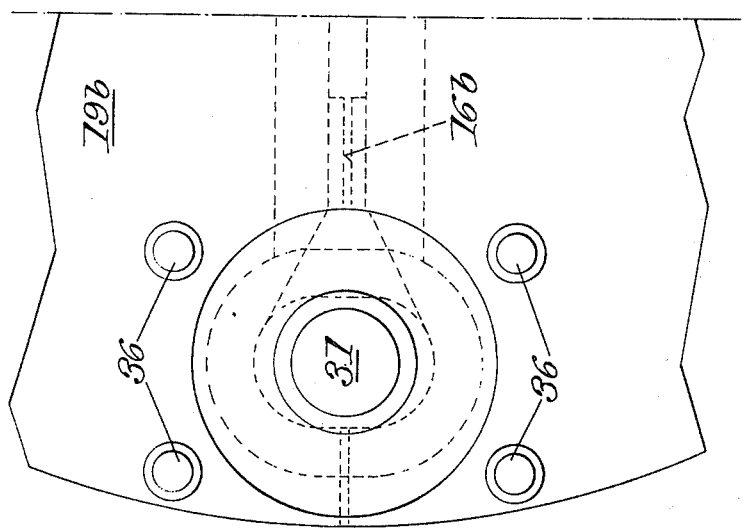
FIG. 6 is a plan view of the device in FIG. 4, after assembly.
Figure 5:
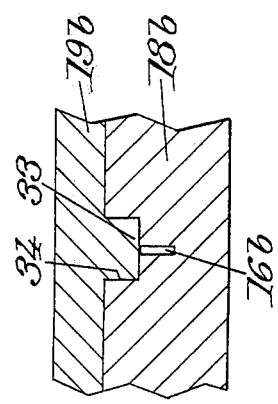
FIG. 5 is a view of a detail in cross-section along line V—V of FIG. 4, after assembly.

Referring to FIGS. 4 – 6 (where, for simplicity, like elements bear like references to FIG. 1) show a modified embodiment which differs mainly in that each cell 15b (or at least some of the cells) is provided with a compartment 31 containing a reagent 32. Referring to FIG. 4, there is shown a bottom plate 18b and a top plate 19b before assembly. Referring to the cross-sectional view in FIG. 5, plate 19b has ribs 33 which are force-fitted in correspondingly-shaped grooves 34 leaving a constricted passage 16b, the width of which usually varies from 1/10th to a few tenths of a millimeter.

Compartments 31 are formed in capsules 34 made of plastics which is deformable but highly resistant to tearing. Capsules 34 are secured, e.g. by gluing, to a thin plastics or metal strip 35 which tears when pressure is exerted on the top wall of a capsule. Strip 35 and the capsules are held in position by stubs 36 which are distributed around each cell 15b and engage in corresponding apertures formed in strip 35 and the capsule strip. The stubs may also engage in the apertures of a strip 21b bearing labels.

The device shown in FIGS. 4–6 is of particular interest for chemical measurements, more particularly for detecting abnormal proportions of constituents in organic liquids such as blood or urine, for detecting enzymes or the like. In such cases it is frequently necessary to use two reagents which cannot be stored together. One is then placed in cell 15b and the other in compartment 31. It may also be necessary to add an additional reagent for detection: it is again stored in compartment 31. The additional reagent may e.g. be necessary to inhibit or indicate the reaction; it may be an accelerator to be introduced at the last moment; it may be a light density solvent for collecting coloured products just under the liquid free level, etc.

Many other modified embodiments of expendable devices according to the invention are possible. When used for medical purpose, the device is used once only and then destroyed. In an embodiment for chemical use, all cells 15 may contain a same reagent and the closure means having a single closable lateral aperture and a lower end wall. The closure means has been inserted into the casing so that its aperture registers with an aperture in the casing. Operation is then the same as before, the pocket being used as a pipette for storing a predetermined volume and transfering it to the corresponding cell. Next, the closure means is removed and replaced by a second closure means which is positioned opposite another aperture. In this manner, the same reaction can be performed on samples coming from different patients, e.g. for quantitative analysis of urea. Each closure means may have not one but two or three apertures, which are located in coincidence with pockets corresponding to cells containing two or three different reagents, e.g. for determining urea and cohlesterol.

Finally, the casing may comprise cells disposed in a number of concentric rows, in which case of course the pockets connecting the cells in the outer row are connected thereto by ducts comprising non-radial portions.

I claim:
1. A device for accurately measuring and dispensing predetermined volumes of a liquid sample, comprising: a casing formed having central axis of rotation, a concentric upwardly open chamber to receive said liquid sample, a plurality of test cells distributed around said chamber and spaced radially therefrom, said cells having transparent walls, and a plurality of radial pockets each having an inner end communicating with said chamber and an outer end communicating with a respective one of said cells by means defining a capillary constriction, each said pocket being located with respect to said chamber for gravity flow of liquid from said cham- ber into said pockets through said respective inner ends;

and displaceable closure means to separate said chamber from said pockets and to retain in each of said pockets, the volumes of liquid passed by gravity from said chamber to said pockets respectively.

2. A device according to claim 1, wherein each said pocket is laterally limited by vertical walls which are substantially parallel and radial with respect to the axis and which are separated by a distance of from 1 to 5 mm.

3. A device according to claim 2, wherein each said pocket has an upper wall which is substantially flat and a lower wall which is upwardly concave, at least over most of its extent.

4. A device according to claim 1, in which all cells are disposed at equal distances from the axis and are connected to concentric chamber by pockets having identical volumes.

5. A device according to claim 1, having a first set of identical cells and associated pockets and at least a second set of identical cells and associated pockets, the pockets of the first set having a volume different from the pockets of the second set.

6. A device according to claim 1, wherein the closure means comprises a cylindrical side wall adapted to be inserted into the chamber to separate it from the pockets, and an end wall adapted to separate the chamber from atmosphere when the closure means is inserted into said chamber.

7. A device according to claim 6, wherein the side wall of the closure means and the chamber are so shaped and proportioned that the closure means is retained in the chamber when manually positioned therein.

8. A device according to claim 6, wherein the side wall of the closure means has a terminal edge arranged to engage the casing to separate the chamber from the pockets.

9. A device according to claim 3, wherein the casing comprises:

a lower plate of transparent rigid material forming said cells, said vertical side walls and lower wall of the pockets and a bottom wall of said chamber, and an upper plate made of plastic material forcibly engaged on to the bottom plate and cooperating therewith to form the constrictions.

10. A device according to claim 1, comprising means to establish a plurality of compartments each located above one cell and each containing a reagent, separated from the cell by a fracturable diaphragm, said compartments being flexible whereby a manual pressure sufficient to break the diaphragm may be exerted thereon.

11. A device according to claim 10, wherein the compartments are of flexible plastics and the diaphragms are formed by a thin film of plastics or metal.

12. A device according to claim 1, wherein each cell contains a dried identification reagent.

13. A method for the measuring and transferring predetermined volumes of a liquid sample, comprising the steps of:

providing a rotatable member defining an upwardly open central chamber concentric with the rotational axis of said member, a plurality of radial pockets communicating at inner ends thereof with said central chamber for gravity flow of liquid from said chamber into each of said pockets, the outer ends of each of said pockets communicating by means of a restriction with each of a plurality of test cells formed in the rotatable member;

filling the central chamber with said liquid sample until the pockets are filled up to said constrictions by gravity flow from said chamber, inserting a closure means to isolate said predetermined volumes of liquid in said pockets and to separate the balance of liquid in said chamber from atmosphere, rotating said device about said rotational axis to create centrifugal forces sufficient to overcome said capillary forces and to casue transfer of said volumes from said pockets into said test cells.

14. A dispensable device for testing antibiotic susceptibility of bacteries in a liquid sample, comprising:

a casing having an axis, an annular wall in said casing defining an upwardly open central chamber, a plurality of radial pockets formed in said casing communicating with said chamber via openings in said annular wall and angularly distributed about said chamber, a plurality of transparent test cells arranged in a circular row around said pockets, means defining a capillary liquid flow restriction connecting each said test cell to a respective one of said pockets, cover means arranged to substantially sealingly engage said annular wall of said chamber and to close said openings while separating said chamber from the ambient atmosphere, each said cell containing a culture medium, at least one antibiotic and a bacterial growth indicator.

* * * * *